(12) United States Patent
Simard et al.

(10) Patent No.: US 11,493,782 B2
(45) Date of Patent: Nov. 8, 2022

(54) MEDICAL DEVICE AND METHOD FOR MANAGEMENT OF OCULAR AXIAL LENGTH GROWTH IN THE CONTEXT OF REFRACTIVE ERROR EVOLUTION

(71) Applicants: Universite de Montreal, Montreal (CA); Patrick Simard, Saint-Laurent (CA); Jean Blanchard, Magog (CA); Remy Marcotte-Collard, Montreal (CA)

(72) Inventors: Patrick Simard, Montreal (CA); Jean Blanchard, Magog (CA); Langis Michaud, Saint-Laurent (CA); Remy Marcotte-Collard, Montreal (CA)

(73) Assignee: Université de Montréal et al., Montreal (CA)

( * ) Notice: Subject to any disclaimer, the term of this patent is extended or adjusted under 35 U.S.C. 154(b) by 110 days.

(21) Appl. No.: 16/763,648

(22) PCT Filed: Nov. 23, 2018

(86) PCT No.: PCT/IB2018/059263
§ 371 (c)(1),
(2) Date: May 13, 2020

(87) PCT Pub. No.: WO2019/102415
PCT Pub. Date: May 31, 2019

(65) Prior Publication Data
US 2020/0363654 A1    Nov. 19, 2020

Related U.S. Application Data

(60) Provisional application No. 62/590,388, filed on Nov. 24, 2017.

(51) Int. Cl.
G02C 7/06    (2006.01)
G02C 7/04    (2006.01)
A61F 2/16    (2006.01)

(52) U.S. Cl.
CPC ............ G02C 7/044 (2013.01); A61F 2/1618 (2013.01); G02C 7/06 (2013.01); G02C 2202/24 (2013.01)

(58) Field of Classification Search
CPC ..... G02C 7/047; G02C 7/041; G02C 2202/24
(Continued)

(56) References Cited

U.S. PATENT DOCUMENTS 5,864,379 A    1/1999  Dunn
6,899,425 B2   5/2005  Roffman et al.
(Continued)

FOREIGN PATENT DOCUMENTS

EP          0480748 A1    4/1992
WO      WO 2001/35880    5/2001
WO      WO 2008/111856   9/2008

OTHER PUBLICATIONS

Contact Lens Spectrum—Defining a Strategy for Myopia Control—A systematic approach can help practitioners more effectively implement—myopia control into practice—By Langis Michaud, OD, MSC, FAAO (Dipl), FSLS, FBCLA; Patrick Simard, OD, MBA, MSC, FAAO; & Rémy Marcotte-Collard, OD—Mar. 1, 2016.

(Continued)

Primary Examiner — Darryl J Collins
(74) Attorney, Agent, or Firm — Fasken Martineau Dumoulin, LLP; Serge Lapointe

(57) ABSTRACT

There is described a medical device for management of the axial length growth of an eye of a subject. The device comprises a central region having a first power, a transition (Continued)

region surrounding the central region, and a peripheral region surrounding the transition region and having a second power. The transition region has a width at most equal to 1.5 mm. The second power is chosen based on the first power to achieve a target net power, the target net power being the addition of the first power and the second power. The surface area of the central and peripheral regions is chosen as a function of the surface area of the pupil of the eye. Furthermore, the curve of power within the transition region is steep between the first power and the second power so that the transition region generates no optically usable power.

20 Claims, 4 Drawing Sheets

(58) Field of Classification Search
USPC .......... 351/159.07, 159.12, 159.22, 159.23, 351/159.78, 159.79
See application file for complete search history.

(56) References Cited

U.S. PATENT DOCUMENTS

| | | | |
|---|---|---|---|
| 8,684,520 B2* | 4/2014 | Lindacher | G02C 7/028 351/159.52 |
| 9,423,633 B2 | 8/2016 | Ho et al. | |
| 2014/0211147 A1* | 7/2014 | Wei | G02C 7/06 351/159.79 |
| 2015/0219926 A1* | 8/2015 | Fujikado | G02C 7/04 351/159.06 |
| 2015/0316788 A1* | 11/2015 | Holden | G02C 7/041 351/159.42 |
| 2016/0054587 A1* | 2/2016 | Brennan | G02C 7/06 623/6.11 |
| 2017/0038603 A1 | 2/2017 | Holden et al. | |

OTHER PUBLICATIONS

International Search Report and Written Opinion for Int. App. No. PCT/IB2018/059263 dated Mar. 21, 2019.

* cited by examiner

MEDICAL DEVICE AND METHOD FOR MANAGEMENT OF OCULAR AXIAL LENGTH GROWTH IN THE CONTEXT OF REFRACTIVE ERROR EVOLUTION

CROSS REFERENCE TO RELATED APPLICATIONS

This application is a U.S. National Phase of International PCT application No. PCT/IB2018/059263 filed on Nov. 23, 2018, which claims the benefit of U.S. Provisional Application No. 62/590,388 filed on Nov. 24, 2017, the contents of each application hereby incorporated by reference in their entirety.

TECHNICAL FIELD

The present invention relates to the field of ocular medical devices and methods for treating a refractive error, and more particularly to medical devices and medical methods for managing the growth of ocular axial length.

BACKGROUND

Myopia is a current refractive error characterized by the perception of blurred images at a distance. Deemed commonplace a few years ago, this refractive error is now considered as a significant risk factor for the development of ocular pathologies over time. In fact, the World Health Organization (WHO) warned in 2016 public health agencies about the increased prevalence of myopia around the world, its occurrence at a younger age and its increasing severity, which may lead to diseases like glaucoma, retinal detachment and macular or choroidal neovascularization.

The WHO took into account the fundamental research results published within the last 10 years, which demonstrate that higher levels of myopia (over −5 diopters) and/or longer axial lengths (over 26 mm) represent significant risk factors to develop conditions that may impact ocular health and visual acuity over time.

It also suggests different clinical strategies, which have shown successful outcomes in slowing the rate of progression of myopia and/or axial length. These interventions can be summarized in 3 categories: lifestyle management, visual and optical management, and pharmacological treatments.

Lifestyle management promotes outdoor activities for a minimum of 45 minutes per day, but preferably two hours, notably before myopia onset. It also addresses the use of computer, tablets, and near work, as well as lightning conditions and other ergonomic aspects related to school or office work soliciting near vision. Visual interventions aim to correct any binocular vision issues revealed during an eye examination, especially the following elements: phoria (natural eye deviation) at near, accommodation/convergence ratio and the lag of accommodation. Orthoptics, vision therapy and optical devices can be used, alone or in conjunction, to fix binocular vision problems. It was demonstrated that the presence of a balanced and unaltered binocular vision is protective against myopia occurrence and its evolution.

Any issue related to accommodation may be treated with the use of optical devices designed with an add section providing an add-power. Consequently, the presence of any of these anomalies may impact on the selection and the design of optical devices used to manage myopia and axial length. For example, a given individual showing a high lag of accommodation (e.g. >+1.25 diopter) and being non-responsive to vision therapy would be compensated with a pair of glasses or contact lenses displaying an add-power between +1.50 diopters and +2.50 diopters. The same device can be used to control or correct myopia but the add section may be used to restore its natural accommodation. In such cases, the add-power should be increased significantly to address both needs.

Optical strategies are based on the fact that rays of light entering the eye should be focused parallel or in front of the peripheral retina instead of behind it, as is the case with regular glasses or contact lenses. This goal is more difficult to achieve with the use of glasses, but is very feasible in contact lenses.

Two types of contact lenses are used, the first being a rigid contact lens, worn overnight, and fitted with a philosophy called orthokeratology (OK). In fact, this lens helps to mold the cornea and to reshape it in order to influence the peripheral refraction. If well designed, OK lenses are well tolerated and are not associated with a higher risk compared to extended wear with soft lenses. The second option highlights the use of soft multifocal contact lenses worn during the day. While these lenses were mostly designed to correct adult presbyopia, distance centered lenses, and at a lesser extent near-centered multifocal lenses were also found to be efficient to control, in part, myopia progression. Most of the current designs of multifocal lenses are limited in the add-power they provide (+0.50 diopter to +3.00 diopters). Their design also varies. For example, some designs use fixed zones. In such cases, commercial designs with higher add powers are associated with blur at distance, which is not suitable. To limit this effect, the central zone should be designed larger or the add power should be limited to +2 diopters. Another strategy is to over-minus the patient (i.e. provide a lens power for distance being higher than the refraction of the patient), which may be detrimental for binocular vision equilibrium and with unknown long-term effect on myopia progression. Other designs generate presbyopic correction with an increase in the add-power from the center to the periphery (positive asphericity), following a constant increase. Furthermore, some new lens designs are based on the principle of extended depth of focus to correct presbyopia. These new lens designs are generating high add-power and are pupil-independent. They were used successfully, off-label, to manage myopia. All of these prior art lenses cannot usually be customized, with a few exceptions.

Further, the pharmacological approach implies the use of commercially available (atropine @ up to 1% concentration) or compound medication (atropine @ 0.01%-@ 0.5% concentration, dosed 1 drop daily) or other drugs, not commercially available, like pirenzepine. Atropine mechanism of action is not fully understood but clinical results have shown the highest efficacy amongst all strategies used to control myopia or axial length progression, especially at higher concentration (1%). Because the long-term safety has not yet been studied, and because of numerous side and rebound effects if used at higher concentration, its use is reserved when optical interventions cannot be considered or achieved, or as an adjunct therapy when applied means fail to achieve a successful control.

While they are functional, these strategies have a limited efficiency (usually between 30 and 50% control in average).

Therefore, there is a need for improved medical devices and methods for managing refractive error evolution or axial length growth.

SUMMARY

According to a first broad aspect, there is provided a medical device for management of an axial length growth of an eye of a subject, the eye having a pupil, the device comprising: a central region having a first power; a transition region surrounding the central region and having a width at most equal to 1.5 mm; and a peripheral region surrounding the transition region, the peripheral region having a second power, wherein a surface area of each one of the central and peripheral regions is chosen as a function of a surface area of the pupil of the eye.

In one embodiment, the surface area of the pupil of the eye corresponds to a surface area of the pupil of the eye evaluated in photopic condition, when the subject is looking at distance with uncovered eyes.

In one embodiment, the central and peripheral regions are adapted to treat at least one of myopia and astigmatism.

In one embodiment, a surface area of the central region and the transition region is comprised between about 20% and about 40% of the surface area of the pupil of the eye.

In one embodiment, the first power of the central region is comprised between about −0.25 diopter and about −30 diopters for said myopia and between about −0.25 diopter and about −10 diopters for said astigmatism.

In one embodiment, the second power of the peripheral region is determined as a function of a target net power and the first power of the central region.

In one embodiment, the target net power is comprised between about +3.5 diopters and about +10 diopters, and the second power is comprised between about +3.75 diopters and about +20 diopters.

In one embodiment, the target net power is equal to about +5 diopters.

In another embodiment, the central and peripheral regions are adapted to treat hyperopia.

In one embodiment, a surface area of the central region and the transition region is comprised between about 30% and about 50% of the surface area of the pupil of the eye.

In one embodiment, the first power of the central region is comprised between about +0.25 diopter and +25 diopters.

In one embodiment, the second power of the peripheral region is determined as a function of a target net power and the first power of the central region.

In one embodiment, the target net power is comprised between about −3.5 diopters and about −10 diopters and the second power of the peripheral region is comprised between about −3.75 diopters and −20 diopters.

In one embodiment, the target net power of the peripheral region is equal to about −5 diopters.

In a further embodiment, the central and peripheral regions are adapted to treat presbyopia.

In one embodiment, the medical device corresponds to a distance-centered device.

In one embodiment, a surface area of the central portion and the transition portion is comprised between about 20% and about 30% of the surface area of the pupil of the eye.

In one embodiment, the first power of the central region is comprised between about −30 diopters and about +25 diopters.

In one embodiment, the peripheral region is provided with an add-power comprised between about +0.25 diopter and about +5 diopters.

In one embodiment, the add-power of the peripheral region is equal to about +2.5 diopters.

In another embodiment, the medical device corresponds to a near-centered device.

In one embodiment, a surface area of the central portion and the transition portion is comprised between about 10% and about 30% of the surface area of the pupil of the eye.

In one embodiment, the second power of the peripheral region is comprised between about −30 diopters and +25 diopters.

In one embodiment, the central region is provided with an add-power comprised between about +0.25 diopters and about +5 diopters.

In one embodiment, the add-power of the central region is equal to about +2.5 diopters.

In one embodiment, the second power is constant throughout the peripheral region.

In another embodiment, the peripheral region comprises a plurality of angular sections each having a respective power.

In one embodiment, two adjacent ones of the plurality of angular sections are provided with different powers.

In one embodiment, the respective power is equal to one of the first power of the central region and the second power of the peripheral region.

In one embodiment, the medical device further comprises an external region surrounding the peripheral region.

In one embodiment, the medical device further comprises a transition region comprised between the peripheral region and the external region, a width of the transition region being at most equal to about 1.5 mm.

In one embodiment, the external region comprises a plurality of angular sections each having a respective power.

In one embodiment, two adjacent ones of the plurality of angular sections are provided with different powers.

In one embodiment, the respective power is equal to one of the first power of the central region and the second power of the peripheral region.

In one embodiment, the external region is divided into an even number of said angular sections.

In one embodiment, the medical device is a corrective lens.

In one embodiment, the corrective lens is a contact lens.

In one embodiment, the contact lens is a soft contact lens.

In another embodiment, the contact lens is one of a rigid lens, a gas permeable lens and a hybrid lens.

In one embodiment, the corrective lens is an intraocular lens.

According to another broad aspect, there is provided a method for treating a condition of an eye of a subject, the method comprising: determining a refractive error of the eye of the subject; determining and a surface area of a pupil of the eye; and providing the medical device described above.

According to a further broad aspect, there is provided a medical device for management of an axial length growth of an eye of a myopic subject, the eye having a pupil, the device comprising: a central region having a first power for adjusting a vision at distance; a transition region surrounding the central region and having a width at most equal to 1.5 mm; and a peripheral region surrounding the transition region, the peripheral region having a second power, wherein a surface area of the central region and the transition region is comprised between about 20% and about 40% of the surface area of the pupil of the eye, and wherein the first power of the central region is comprised between about −0.25 diopter and about −30 diopters.

In one embodiment, the surface area of the pupil of the eye corresponds to a surface area of the pupil of the eye evaluated in photopic condition, when the subject is looking at distance with uncovered eyes.

In one embodiment, the second power of the peripheral region is determined as a function of a target net power and the first power of the central region.

In one embodiment, the target net power is comprised between about +3.5 diopters and about +10 diopters, and the second power is comprised between about +3.75 diopters and about +20 diopters.

In one embodiment, the target net power is equal to about +5 diopters.

In one embodiment, the second power is constant throughout the peripheral region.

In another embodiment, the peripheral region comprises a plurality of angular sections each having a respective power.

In one embodiment, two adjacent ones of the plurality of angular sections are provided with different powers.

In one embodiment, the respective power is equal to one of the first power of the central region and the second power of the peripheral region.

In one embodiment, the medical device further comprises an external region surrounding the peripheral region.

In one embodiment, the medical device further comprises a transition region comprised between the peripheral region and the external region, a width of the transition region being at most equal to about 1.5 mm.

In one embodiment, the external region comprises a plurality of angular sections each having a respective power.

In one embodiment, two adjacent ones of the plurality of angular sections are provided with different powers.

In one embodiment, the respective power is equal to one of the first power of the central region and the second power of the peripheral region.

In one embodiment, the external region is divided into an even number of said angular sections.

In one embodiment, the medical device is a corrective lens.

In one embodiment, the corrective lens is a contact lens.

In one embodiment, the contact lens is a soft contact lens.

In another embodiment, the contact lens is one of a rigid lens, a gas permeable lens and a hybrid lens.

In one embodiment, the corrective lens is an intraocular lens.

According to still another broad aspect, there is provided a method for treating a condition of an eye of a subject, the method comprising: determining a refractive error of the eye of the subject; determining and a surface area of a pupil of the eye; and providing the medical device described above.

According to still a further broad aspect, there is provided a method for managing of an axial length growth of an eye of a subject, comprising: creating a central region within a cornea of the eye of the subject, the central region having a first power; creating an intermediate region surrounding the central region within the cornea of the eye, the intermediate region having a width at most equal to about 1.5 mm; and creating a peripheral region surrounding the intermediate region within the cornea of the eye, the peripheral region having a second power, wherein a surface area of each one of the central and peripheral regions is chosen as a function of a surface area of the pupil of the eye.

In one embodiment, the step of creating the central, intermediate and peripheral regions comprises propagating a beam of a laser on the cornea of the eye.

In one embodiment, the central and peripheral regions are adapted to treat at least one of myopia and astigmatism.

In one embodiment, a surface area of the central region and the transition region is comprised between about 20% and about 40% of the surface area of the pupil of the eye.

In one embodiment, the first power of the central region is comprised between about −0.25 diopter and about −30 diopters for said myopia and between about −0.258 diopter and about −10 diopters for said astigmatism.

In one embodiment, the second power of the peripheral region is determined as a function of a target net power and the first power of the central region.

In one embodiment, the target net power is comprised between about +3.5 diopters and about +10 diopters, and the second power is comprised between about +3.75 diopters and about +20 diopters.

In one embodiment, the target net power is equal to about +5 diopters.

In another embodiment, the central and peripheral regions are adapted to treat hyperopia.

In one embodiment, a surface area of the central region and the transition region is comprised between about 30% and about 50% of the surface area of the pupil of the eye.

In one embodiment, the first power of the central region is comprised between about +0.25 diopter and +25 diopters.

In one embodiment, the second power of the peripheral region is determined as a function of a target net power and the first power of the central region.

In one embodiment, the target net power is comprised between about −3.5 diopters and about −10 diopters and the second power of the peripheral region is comprised between about −3.75 diopters and −20 diopters.

In one embodiment, the target net power of the peripheral region is equal to about −5 diopters.

In a further embodiment, the central and peripheral regions are adapted to treat presbyopia.

In one embodiment, a surface area of the central portion and the transition portion is comprised between about 20% and about 30% of the surface area of the pupil of the eye.

In one embodiment, the first power of the central region is comprised between about −30 diopters and about +25 diopters.

In one embodiment, the peripheral region is provided with an add-power comprised between about +0.25 diopter and about +5 diopters.

In one embodiment, the add-power of the peripheral region is equal to about +2.5 diopters.

In another embodiment, a surface area of the central portion and the transition portion is comprised between about 10% and about 30% of the surface area of the pupil of the eye.

In one embodiment, the second power of the peripheral region is comprised between about −30 diopters and +25 diopters.

In one embodiment, the central region is provided with an add-power comprised between about +0.25 diopters and about +5 diopters.

In one embodiment, the add-power of the central region is equal to about +2.5 diopters.

In one embodiment, the second power is constant throughout the peripheral region.

In another embodiment, said creating the peripheral region comprises creating a plurality of angular sections within the peripheral region, each one of the plurality of angular sections having a respective power.

In one embodiment, two adjacent ones of the plurality of angular sections are provided with different powers.

In one embodiment, the respective power is equal to one of the first power of the central region and the second power of the peripheral region.

In one embodiment, the method further comprises the step of creating an external region surrounding the peripheral region.

In one embodiment, the method further comprises the step of creating a transition region comprised between the peripheral region and the external region, a width of the transition region being at most equal to about 1.5 mm.

In one embodiment, the external region comprises a plurality of angular sections each having a respective power.

In one embodiment, two adjacent ones of the plurality of angular sections are provided with different powers.

In one embodiment, the respective power is equal to one of the first power of the central region and the second power of the peripheral region.

In one embodiment, the external region is divided into an even number of said angular sections.

In the following, it should be understood that a first power expressed in diopters is associated with the central region and a second and different power also expressed in diopters is associated with the peripheral region.

The power of the central region refers to the power equivalent to the refractive error at distance of the subject.

The power of the peripheral region refers to the power added to the power of the central region. The power of the peripheral region may be chosen so as to achieve a target net power determined to be efficient to control myopia progression or axial length elongation in a given subject. The power of the peripheral region is analogous to an add-power in a case of a presbyopic subject.

The net power refers to the addition of the power of the central region and the power of the peripheral region.

The net power may be referred to as a net plus power when it is corresponds to the addition of a convex power in the peripheral region, that is higher than the negative power of the central region, in the case of a lens designed to control myopia/astigmatism and/or axial length.

The net power may be referred to as a net minus power when it corresponds to the addition of a concave power in the peripheral region, that is higher than the positive power of the central region, in the case of a lens designed to control hyperopia and/or axial length.

The add-power refers to the addition of a convex power in the peripheral region in the case of a lens designed to correct presbyopia, independently of whether the central region is provided with a positive or negative power.

The peripheral region may be designed according to a target power or a target net power. When a target net power is set for the peripheral region, the power of the peripheral region is obtained by subtracting the power of the central region from the net power of the peripheral region.

In the following, power values associated with astigmatism are expressed as negative numbers following the standard in optometry. However, the person skilled in the art will understand that if one would like to follow the standard in ophthalmology, then positive values should be used for the powers.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
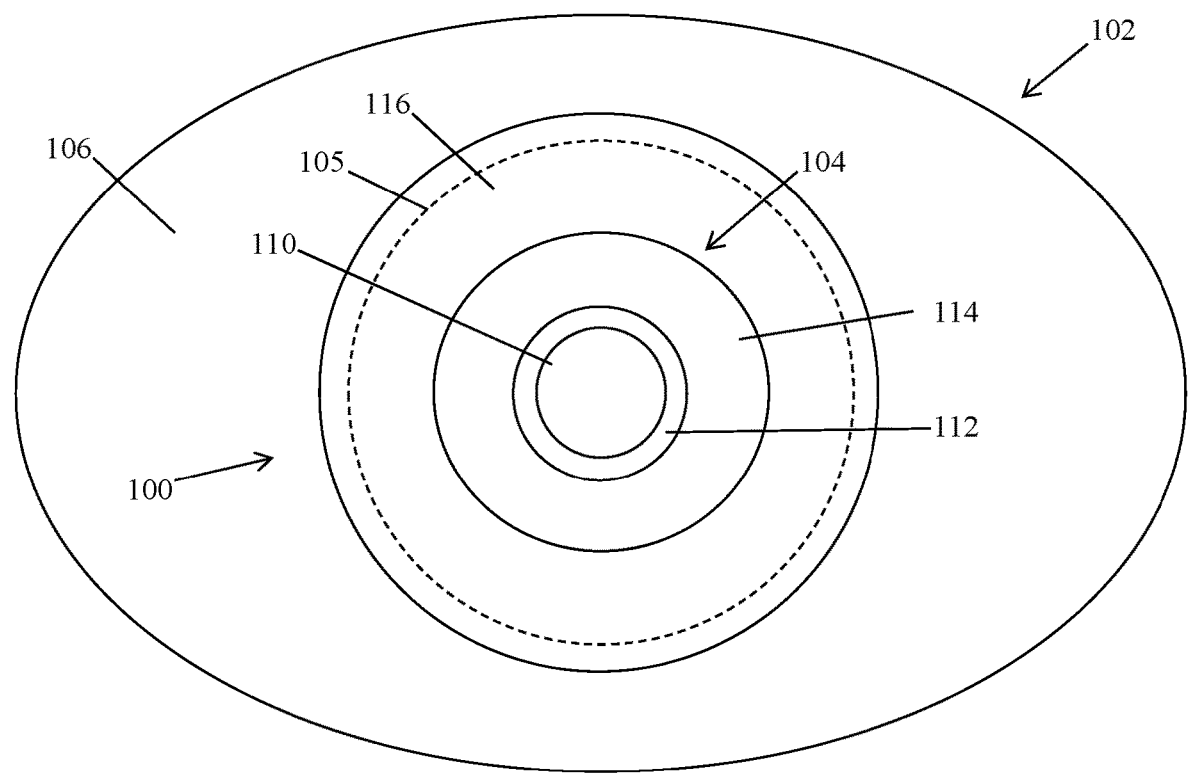
FIG. 1 illustrates a medical device for treating a refractive error comprising a central region, an intermediate region and a peripheral region, the surface area of the medical device being equal to that of the pupil, in accordance with an embodiment.

In the following, there is described a medical device for managing the axial length growth of an eye, a method of medical treatment for managing the axial length growth of an eye and a method for selecting an adequate medical device for managing the ocular axial length growth of an eye. The present medical device and method may be used for treating refractive errors such as myopia, hyperopia, astigmatism and/or presbyopia.

The inventors discovered that it is important to focus on the ocular axial length evolution first, as a response to multifactorial stimuli such as peripheral refraction. In fact, when it grows, an eye becomes elongated, and usually the crystalline lens present inside of the eye modifies its shape and the volume of the anterior and the posterior chamber may vary also in order to adapt to this elongation. This process is called emmetropization. For subjects suffering from myopia, or hyperopic subjects, this emmetropization process is no longer functioning normally as if the biofeedback between the retina and the other structures of the eye seems to be lost, altered or broken. According to the inventors, myopia should, therefore, be considered as the clinical measurable effect of the axial length elongation, in absence of efficient emmetropization. Moreover, myopia may be considered as being a significant risk factor for the development of ocular pathology when it reaches a level over −6 diopters or 26 mm in axial length.

Most of the prior art techniques for managing myopia focus on the myopia progression, i.e. the diopters change over time, without looking at the underlying causative mechanism, which is the variation of the ocular axial length, not compensated by a modification of the shape and/or the power of the lens. Consequently, according to the inventors, a device or a method for managing myopia should be efficient at managing first the ocular axial length progression, and then the refractive error evolution.

Analysis made on the corneal surface, through topography, revealed that, in the case of myopia and/or astigmatism, Ortho-K lenses flatten the central cornea, using positive hydraulic pressure from the compressed tear film under the lens. This defines zone A, which is surrounded by a steeper zone generated by negative hydraulic pressure on the epithelial cells, known as zone B. Zone A helps to compensate for refractive error. For example, if it becomes flatter, zone A will compensate for myopia and astigmatism up to a certain amount, limited by the shape of the cornea. To the contrary, zone B is associated with a more convex power, in order of 1 to 1.25 ratio with zone A, or higher if the lens curvatures are customized. The power of the second zone is defined as a net convex (+) power. The add-power of the system represents the difference between the central zone and the peripheral zone. For example, given a cornea with a central curvature of 45 diopters, a standard ortho-K lens generating 3 diopters of flattening will make zone A at 42 diopters and zone B at 49 diopters. In terms of power, this variation is associated with a −3 diopters effect centrally and +4 diopters in zone B. The add-power of this system is then evaluated at 7 diopters. Clinical results indicate that the amount of convex power and the area reached by the net plus power, in the peripheral retina, will influence how myopia and axial length progressions will be affected. The transition of powers, between zone A and zone B can be slow, if a larger transition zone is inserted between them. It can also be abrupt, which means a very rapid transition, with a steep slope between the power generated in zone A and that generated in zone B. In the first case, a slower transition may be used as an optical correction for intermediate distance (40 to 80 cm) or to balance accommodation. In the second case, a rapid transition remains noise for the brain and cannot be used for the optical correction.

The inventors have found that the use of higher net plus powers, and a defined balance between zones A and B diameters based on the pupil area, as well as an abrupt and fast transition between the zones A and B powers, dictate a better outcome.

The inventors have also found that the low add-power of soft multifocal lenses can be less effective to control myopia and axial length evolution, especially in presence of binocular vision issues. They found that the use of higher convex powers for zone B, with current commercial designs, is often associated with blur at distance, generating the need of overcorrecting the patient, which may impact accommodation and convergence. Lens centration is also more problematic for some lenses provided with high add-power, and decentration may alter the outcome because of the misalignment of the lens zones and the visual axis of the eye.

As a result, the inventors have developed a medical device adapted to manage the ocular axial length in order to treat refractive errors such as myopia and hyperopia, with or without astigmatism. Based on the same principles but with adaptation of the powers, this device may be also used to correct presbyopia, with no impact on the axial length. The medical device is adapted to be worn by a subject or user. For example, the medical device can be worn directly on the surface of the ocular surface of the subject. The medical device comprises three sections or portions, i.e. a central portion, an intermediate or transition portion and a peripheral portion. The lens power or power of the central portion is chosen as a function of the refractive error to be treated in order to adjust the vision at distance of the eye of the subject, without creating central blur. The peripheral portion presents a different power relative to the central portion and is adapted to influence the peripheral refraction. In one embodiment, the power value remains substantially constant through the peripheral portion. This implies that the power of the peripheral portion varies relatively to the power of the central portion. For example, for a net plus power of +5 diopters, the power of the peripheral region is +8 diopters considering a power of −3 diopters for the central region but will be +8.5 diopters if the central region power is equal to −3.5 diopters. In one embodiment, the sum of the central region power and the peripheral region power corresponds to a predefined number, known as the net power of the peripheral region or the net plus power when it is positive. In one embodiment, the net plus power ranges from +2 diopters to +20 diopters. In the case of hyperopia, the net power is negative and is referred to as the net minus power. In one embodiment the net minus power ranges between −2 diopters and −20 diopters. For example, a given lens may be designed with a central region power of +4 diopters and a peripheral region power of −10 diopters if the net minus power was set to −6 diopters. If the central zone power is changed to +5 diopters, the power of the peripheral region will be set to −11 diopters.

In the case of myopia and hyperopia, the peripheral region power value is selected not to interfere with the natural accommodative process. Consequently, the net power of the peripheral region should exceed 3.5 diopters, i.e. +3.5 diopters in the case of myopia and −3.5 diopters for hyperopia. In the case of presbyopia, the peripheral region power value may be considered as an addition to the distance power and is selected to correct vision at near distance. In this case, the net power of the peripheral region may range from +0.5 diopter to +5 diopters. The surface areas of the three regions are chosen as a function of the surface area of the pupil and the width of the intermediate portion is chosen so that the transition of powers between central and peripheral portion be abrupt.

In the case of myopia, the inventors have found that smaller diameters for central regions (zones A) combined with larger diameters peripheral regions (zones B) are indicated for fast progressors (>0.75 diopter/year) because such subjects need a larger area of net plus power in the optical system to get a better control. Furthermore, larger diameters for central regions are indicated when myopia or axial length tend to be stabilized, or if the vision distance is too much impacted wearing lenses designed with smaller diameter central regions. Consequently, in the case of myopia, the surface area of the section comprising the central region and the intermediate region should range between 20% and 40% of the entire pupil area.

In the case of hyperopia, the same rationale may apply, to the exception that a larger central region is needed to alleviate blur at distance. Consequently, the surface area of the section comprising the central region and the intermediate region should range between 30% and 50% of the entire pupil area.

In both cases, the transition should not generate a power that is optically usable by the visual system. This implies that the progression from the central region to the peripheral region should be fast and abrupt, and the slope of the power curve should be the steepest possible in the intermediary region. This also implies that the width of the intermediary region should be kept as minimal as possible. In one embodiment, the width of the intermediary region should be less than 1.5 mm. For example, the width of the intermediary region may range from about 0.1 mm to about 1.5 mm.

The width of the peripheral zone is determined by the overall optic zone diameter of the lens. In general, the optic zone diameter of the lens varies from about 6 mm to 8 mm, according to the design, the material, the overall diameter of the lens, the power of the lens and the corrective goal of the device.

Consequently, the medical device may be designed as follows:

Width of the optic zone of the lens=central region width+intermediary region width+peripheral region width.

For example, given an optical zone of about 8.0 mm, the width of the central region may be equal to about 2.2 mm, the width of the intermediary region may be equal to about 0.5 mm and the width of the peripheral may be equal to about 5.30 mm. In another example for high myopia and given an optical zone of about 6 mm, the width of the central region may be equal to about 2.27 mm, the width of the intermediate region may be equal to about 1 mm and the width of the peripheral may be equal to about 2.73 mm, in the case of an add power superior to +10 diopters.

In one embodiment, the medical device is a corrective lens adapted to treat myopia or hyperopia, or presbyopia, with or without astigmatism. The corrective lens may be a contact lens such as a soft lens or a rigid lens, a gas permeable lens or a hybrid lens. An hybrid lens is defined as a contact lens of which the center is rigid or rigid gas permeable and surrounded by a soft supportive skirt. The skirt may be made of hydrogel, silicone-hydrogel, or any other approved material, and the hybrid lens may be manufactured as a single unit. In another embodiment, the corrective lens may also be an intraocular lens.

FIG. 1 illustrates one embodiment of a medical device 100 for managing the axial length growth of an eye 102. The eye 102 comprises a pupil 104, a cornea 105, an iris (not shown) and a sclera 106. At least the pupil 104 and the visible iris are covered by the cornea 105.

The medical device 100 is adapted to be positioned centrally over the cornea 105, and more precisely in front of at least the geometric center of the pupil 104. In one embodiment, the medical device 100 may be in physical contact with the ocular surface, i.e. the surface of the eye 102, once positioned.

The medical device 100 comprises a central region 110, an intermediate region 112 and a peripheral region 114. The central region 110 is substantially circular while the intermediate and peripheral regions 112 and 114 each have an annular shape. The intermediate region 112 extends radially from the central region 110 along a first width and the peripheral region 114 extends from the intermediate region 112 along a second and different width. Once the medical device is installed on the subject, the center of the central section 110 and the center of the pupil 104 overlap each other so that the medical device 100 is centered on the pupil 104. In one embodiment, the optimal fit implies that the optical axis of the medical device coincides with the visual axis of the eye, which may differ slightly from the geometric center.

The power of the central region 110 is chosen as a function of the type of refractive error to be treated and characteristics of the subject in order to adjust the vision at distance of the subject. The power of the peripheral region 114 is chosen so as to influence the peripheral refraction (myopia and hyperopia) or to correct vision at near (presbyopia). When the medical device 100 is adapted to manage myopia, the peripheral region 114 provides a power value being more convex than the central region power. When the medical device 100 is adapted to manage hyperopia, the peripheral region 114 provides a power value being more concave than the central region power. The intermediate region 112 does not have an effective power but facilitates the transition between distance and peripheral regions. This surface varies rapidly from the power value of the central region 110 to the power value of the peripheral region 114. The width of the intermediate region 112 is chosen so that the transition between distance and peripheral powers be abrupt, with the steepest possible slope and the smallest possible width as for the power profile. In one embodiment, the width of the intermediate region 112 is equal to or less than 1.5 mm.

In one embodiment, the power of the peripheral region 114 is comprised between +3.75 diopters and +20 diopters if the central region power is negative and used for myopia and/or astigmatism control In another embodiment, the power of the peripheral region 114 is comprised between −3.75 diopters and −20 diopters if the central region power is positive and used for hyperopia control. In one embodiment, such a value of power for the peripheral region 114 associated with a minimal width of about 0.1 mm to a maximal width of about 1.5 mm for the intermediate region 112 ensures an abrupt power variation between the central region 110 and the peripheral region 114.

Presbyopic patients have, in general, smaller pupils, which constrict even more when reading or looking at close distance. For this reason, a smaller central region should be designed for distance vision to provide a greater peripheral region and a greater add-power area in the system for the presbyopic correction. Another reason is that the design, when used for presbyopia, does not aim to alter axial length neither to modify refractive error evolution over time. Consequently, the balance between distance and near power, and their relative areas, should be different compared to myopia or hyperopia management Consequently, for the correction of presbyopia and in a design referred to as distance-centered, the power of the peripheral region 114 is chosen so that the peripheral region 114 provides an add-power that may range from +0.25 diopter to +5 diopters, relative to the power of the central region 110, which are the usual add-power found for emergent to mature presbyopes. Add-power values higher than +3.00 may be needed for specific very precise tasks at close distance. For example, an add-power value of +5 diopters may be needed by someone needing precise vision at 20 cm. The central region area may vary from 20 to 30% of the pupil area. Alternatively, in a design referred to as near-centered, the power of the central region may be chosen so that the central region 110 provides an add-power that may range from +0.25 diopter to +5 diopters, relative to the power of the peripheral region 114.

In the illustrated embodiment, the three regions 110, 112 and 114 of the medical device 100 lie totally or in part on the pupil 104 so that the medical device 100 may overlap the pupil 104 once the medical device has been installed on the subject. The surface area of the different regions 110, 112 and 114 of the medical device 100 is chosen as a function of the surface area of the pupil 104 of the eye 102 to be treated. In one embodiment, the surface area of the pupil is assessed using an electronic or manual device, as known in the art, under photopic conditions while the patient is looking at distance and the eyes are not covered. The surface area of each region 110, 112, 114 is chosen so as to cover a given percentage of the surface area of the pupil 104 when the medical device 100 is installed on the subject, e.g. when the medical device 100 is installed on the eye 102 of the subject. The percentage of the surface area of the pupil 104 covered by each region 110, 112, 114, the power of the central region 110 and the power of the peripheral region 114 (as long as the peripheral region power is comprised between about +3.75 diopters and about +20 diopters for myopes or between about −3.75 diopters and about −20 diopters for hyperopes or the add-value is comprised between +0.25 diopter and +5 diopters for presbyopes) are chosen as a function of the refractive error to be treated, its evolution over time and/or some characteristics of the subject such as the dimensions (diameter) of the pupil 104 of the subject and the refraction of the eye of the subject. For any refractive error and any subject, the power of the peripheral region 114 is comprised between about +3.75 diopters and about +20 diopters (myopic eye), between about −3.75 diopters and about −20 diopters (hyperopic eye) or chosen so that the add-value of the peripheral region 114 is comprised between +0.25 diopters and about +5.00 diopters for presbyopic eye, and the width of the intermediate region 112 is chosen to be at most equal to 1.5 mm to ensure an abrupt variation of power between the central and peripheral regions 110 and 114.

While the present medical device may be fully customized for each subject, based on individual parameters, it may be possible to offer a more practical option by averaging the customization process. More precisely, the inventors have determined, after studying various populations, that for a myopic subject showing a pupil diameter between about 4 mm and about 5 mm, the central region would be 5.03 about mm$^2$, while subjects with pupil diameter from about 5.1 mm to about 6.4 mm, would be initially fit with a lens showing a central area of about 8.19 mm$^2$ and finally, if the subject's pupil diameter is at least equal to about 6.5 mm, the central region area would be about 13.27 mm$^2$ at first intention.

While the diameter of the pupil is assessed under photopic conditions while the patient is looking at distance, it should be understood that other methods for determining the diameter of the pupil may be used. For example, the diameter of the pupil may be measured under dim illumination conditions. In this case, a correction factor is applied to the measured pupil diameter to obtain the diameter of the pupil that would have been measured under photopic conditions while the patient is looking at distance. Similarly, if the diameter of the pupil is measured under bright illumination conditions, a correction factor may be applied to the measured pupil diameter to obtain the diameter of the pupil that would have been measured under photopic conditions while the patient is looking at distance.

In one embodiment, the refractive error to be treated is myopia. In this case, the rate of growth of the ocular axial length is to be reduced. The surface area of the section comprising the central region 110 and the intermediate region 112 is chosen to be comprised between about 20% and about 40% of the surface area of the pupil 104 of the eye 102. As a result, the surface area of the peripheral region 114 is comprised between about 60% and about 80% of the surface area of the pupil 104. The power of the central region 110 is comprised between −0.25 diopter and −30 diopters. The power of the peripheral region 114 is comprised between about +3.75 diopters and about +20 diopters to reach a net power for the peripheral region comprised between about +3.5 diopters and about +10 diopters, regardless of the central refractive error. In one embodiment, the net plus power of the peripheral region 114 is about +5 diopters. In this case, a lens powered −2 diopters at distance will be designed with a peripheral power of about +7 diopters. For a lens having a central region power of about −4.00 diopters, a peripheral region power of about +9 diopters would be required to reach a net power of +5 diopters.

For example, for a given subject with −3.00 diopters, evolving by 0.50 diopter/year, and showing a pupil diameter of 5 mm under photopic condition, the pupil area is then 19.64 mm$^2$. The central area may vary from 20% (3.93 mm$^2$) up to 40% (7.85 mm$^2$). In this case, the subject may be fitted with a device designed with central region of −3 diopters of power, to correct distance vision. The area covered by the central region and the intermediary region would have a diameter of 2.74 mm (30% coverage) adjustable to 3.16 mm (40% coverage) if needed. The central region would be surrounded by a peripheral region of a net+power of 5 diopters (=+8 diopters peripheral power), and a width of 5.26 mm (70% coverage) adjustable to 4.84 mm (60% coverage) for the intermediary region (considering a total optic zone diameter of 8 mm), which can be limited if the power of the peripheral region is less than +10 diopters. Another example may be to fit a subject of −8 diopters, known as a fast progressor, showing a pupil diameter of 6 mm, with a lens designed with an area covered by the central region and the intermediary region of 2.68 mm diameter (20%), and a peripheral region of a net power of +5 diopters (i.e. a peripheral region power of +11 diopters) and a width of 4.72 mm for the peripheral region (considering a total optic zone diameter of 8 mm) because of the higher add value.

In an embodiment in which the refractive error to be treated is hyperopia, the rate of growth of the ocular axial length is to be increased. The surface area of the section comprising the central region 110 and the intermediate region 112 is chosen to be comprised between about 30% and about 50% of the surface area of the pupil 104 of the eye 102. As a result, the surface area of the peripheral region 114 is comprised between about 50% and about 70% of the surface area of the pupil 104. The power of the central region 110 is comprised between +0.25 diopter and +25 diopters. The power of the peripheral region 114 is comprised between about −3.75 diopters and about −20 diopters to reach a less convex or more concave value reaching the peripheral retina regardless of the central refractive error. The net minus power of the peripheral region 114 is comprised between about −3.5 diopters and about −10 diopters. In one embodiment, the net minus power of the peripheral region 114 is about −5 diopters. For example, a lens powered +2 diopters at distance (i.e. a central region having a power of +2 diopters) will be designed with a peripheral power of −7 diopters if the constant net power is set at −5 diopters. Another lens of +4 diopters at distance would have to carry a peripheral power of −9 diopters to reach the same net power value of −5 diopters.

The inventors have found that, in the case of hyperopia control and if the area of the central region is less than 30% of the pupil area, the distance vision may be significantly impacted. They also found that over 50% of pupil area for the central region, there is not sufficient effect from the peripheral region. Given a patient of +4 diopters, with a pupil of 4.5 mm, the subject may be fitted with a lens of +4 diopters for the power of the central region with a width of 2.46 mm (30%) for the area covering the central region and the intermediary region (considering an optic zone of 8 mm) and a peripheral region having a net power of −3 diopters (i.e. a peripheral region power of −7 diopters) with a width of 6.04 mm.

In an embodiment in which the refractive error to be treated is astigmatism, the surface area of the section comprising the central region 110 and the intermediate region 112 is chosen to be comprised between about 20% and about 40% of the surface area of the pupil 104 of the eye 102. As a result, the surface area of the peripheral region 114 is comprised between about 60% and about 80% of the surface area of the pupil 104. The power of the central region 110 is comprised between −0.25 diopter and −10 diopters of astigmatism, with or without myopia or hyperopia. The power of the peripheral region 114 is comprised between about +3.75 diopters and about +20 diopters to reach a net power ranging from +3.5 diopters to +10 diopters, regardless of the central refractive error. In one embodiment, the net plus power of the peripheral region 114 is about +5 diopters. For example, in the case of astigmatism, a lens powered −2 diopters at distance will be designed with a peripheral region power of +7 diopters if the constant net power is set at +5 diopters Another lens having a central toric power of −4 diopters would have to carry a peripheral region toric power of +9 diopters to reach the same net plus power value of +5 diopters.

In a first embodiment in which the refractive error to be treated is presbyopia using a distance-centered design, the central region 110 may be used for correcting the distance vision. In this case, the surface area of the section comprising the central region 110 and the intermediate region 112 is chosen to be comprised between about 20% and about 30% of the surface area of the pupil 104 of the eye 102. As a result, the surface area of the peripheral region 114 is comprised between about 70% and about 80% of the surface area of the pupil 104. The power of the central region 110 is comprised between −30 diopter and +25 diopters. The power of the peripheral region 114 is chosen so that the peripheral region 114 provides an add-power comprised between about +0.25 diopters and about +5 diopters, i.e. the power of the peripheral region 114 is comprised between about +0.25 diopters and about +5 diopters. In one embodiment, the add-power of the peripheral region 114 is about +2.5 diopters.

In a second embodiment in which the refractive error to be treated is presbyopia using a near-centered design, the peripheral region 114 is used for correcting the distance vision. In this case, the surface area of the section comprising the central region 110 and the intermediate region 112 is chosen to be comprised between about 10% and about 30% of the surface area of the pupil 104 of the eye 102. As a result, the surface area of the peripheral region 114 is comprised between about 70% and about 90% of the surface area of the pupil 104. The power of the peripheral region 114 is comprised between −30 diopters and +25 diopters. The power of the central region 110 is chosen so that the central region 110 provides an add-power comprised between about +0.25 diopters and about +5 diopters. In one embodiment, the add-power of the central region 114 is about +2.5 diopters.

While in the embodiment illustrated in FIG. 1 the summation of the surface areas of the three regions 110, 112 and 114 is substantially equal to the surface area of the photonic pupil 104, it should be understood that other configurations may be possible. For example, the three regions may have a total surface are that is greater than that of the pupil, as illustrated in FIG. 2.

Figure 2:
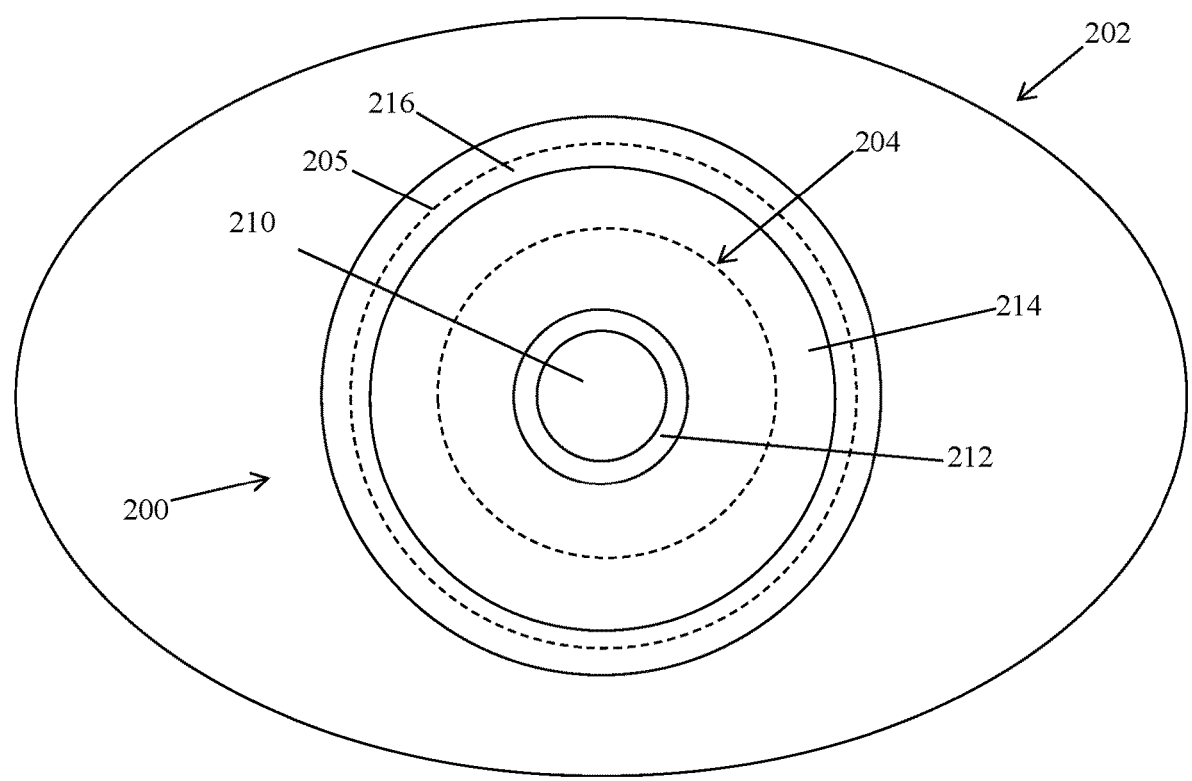
FIG. 2 illustrates a medical device for treating a refractive error comprising a central region, an intermediate region and a peripheral region, the surface area of the medical device being greater than that of the pupil, in accordance with an embodiment.

FIG. 2 illustrates a medical device 200 for treating a refractive error by managing the ocular axial length of an eye 202. In this embodiment, the width (or diameter) of the medical device 200 is greater than the diameter of the cornea 205.

The medical device 200 is adapted to be positioned in front of the eye 202, and more precisely in front of at least the pupil 204. In one embodiment, the medical device 200 may be in physical contact with the ocular surface of the eye 202 once positioned.

The medical device 200 comprises a central region 210, an intermediate region 212 and a peripheral region 214. The central region 210 is substantially circular while the intermediate and peripheral regions 212 and 214 each have an annular shape. The intermediate region 212 extends radially from the central region 210 along a first width and the peripheral region 214 extends from the intermediate region 212 along a second and different width. In this embodiment, the total radius of the medical device 200 which corresponds to the summation of the radius of the central region 210, the width of the intermediate region 212 and the width the peripheral region 214 is greater than the radius of the pupil 204. As a result the surface area of the medical device 200 is greater than that of the pupil 204.

The power of the central region 210 is chosen as a function of the type of refractive error to be treated and characteristics of the subject in order to adjust the vision at distance of the subject. The power of the peripheral region 214 is chosen so as to influence the peripheral refraction in the case of myopic and hyperopic subjects. The power of the peripheral vision is chosen to correct the vision at near and does not influence the axial length, in the case of presbyopic subjects. The transition of power within the intermediate region 212 varies rapidly from the power value of the central region 210 to the power value of the peripheral region 214. The slope of the power transition should be as steep as possible. The width of the intermediate region 212 should be minimal and is chosen along with the value of power of the peripheral region 214 so that the variation of power within the intermediate region 212 be fast and abrupt. In one embodiment, the width of the intermediate region 212 varies from about 0.1 mm to about 1.5 mm, depending on the power of the peripheral region. Power over +10 diopters require larger transition zone while any power below +10 diopters needs to be as small as it is technically possible to achieve.

The surface area of each region 210, 212, 214 of the medical device 200 is chosen as a function of the surface area of the pupil 204 of the eye 202 to be treated. The surface area of each region 210, 212, 214 is chosen so as to cover a given percentage of the surface area of the photopic pupil 204 when the medical device 200 is installed on the subject, e.g. when the medical device 200 is installed on the eye 202 of the subject. For example, the region 210 may vary from 2 mm to 4.2 mm; the region 212 may vary from 0.1 mm to 1.5 mm and the peripheral region 214 may vary from 2.6 mm to 6 mm (considering an optic zone of 8 mm). The percentage of the surface area of the pupil 204 covered by each region 210, 212, 214, the power of the central region 210 and the power of the peripheral region 214 (as long as the power of the peripheral region 214 is comprised between about +3.75 diopters and about +20 diopters for myopia with or without astigmatism or between about −3.75 diopters and about −20 diopters for hyperopia with or without astigmatism or is chosen so that the central region 110 or the peripheral region 214 provides an add-power comprised between +0.25 and +5.00 D for presbyopia with or without astigmatism) are chosen as a function of the refractive error to be treated and some characteristics of the subject such as the diameter of the pupil 204 of the subject and the refraction of the eye of the subject. The power of the peripheral region 214 is chosen so as to provide a fixed net value and depends on the power of the central region 201. For any refractive error and any subject, the power of the peripheral region 214 is comprised between about +3.75 diopters and about +20 diopters (myopia with or without astigmatism) or between about −3.75 diopters and about −20 diopters (hyperopia with or without astigmatism) or the central region or the peripheral region provides an add-power that is comprised between about +0.25 and about +5.00 D (presbyopia with or without astigmatism), and the width of the intermediate region 212 is chosen to be at most equal to 1.5 mm to ensure an abrupt variation of power between the central and peripheral regions 210 and 214.

In one embodiment, the refractive error to be treated is myopia. In this case, the rate of growth of the ocular axial length is to be reduced. In this case, the surface area of the section comprising the central region 210 and the intermediate region 212 is chosen to be comprised between about 20% and about 40% of the surface area of the pupil 204 of the eye 202. Once the medical device 200 is installed on the subject, between about 60% and about 80% of the surface area of the pupil 204 is covered by the peripheral region 214. The power of the peripheral region 214 is comprised between about +3.75 diopters and about +20 diopters and is determined as a function of the power of the central region to obtain a target net power, to be determined. In one embodiment, the net power for the peripheral region 214 is about +5 diopters. In this embodiment, if the central region has a power of −3 diopters, then the power of the peripheral region will be +8 diopters. If the central region has a power of −6 diopters, then the power of the peripheral region 214 will be set at +11 diopters.

In an embodiment in which the refractive error to be treated is hyperopia. In this case, the rate of growth of the ocular axial length is to be increased. The surface area of the section comprising the central region 210 and the intermediate region 212 is chosen to be comprised between about 30% and about 50% of the surface area of the pupil 204 of the eye 202. As a result, the surface area of the peripheral region 214 is comprised between about 50% and about 70% of the surface area of the pupil 204. The power of the central region 210 is comprised between +0.25 diopter and +25 diopters. The power of the peripheral region 214 is comprised between about −3.75 diopters and about −20 diopters and is determined as a function of the power of the central region to obtain a target net power value comprised between about −3.75 diopters and about −10 diopters. The net minus power of the peripheral region 114 is comprised between about −3.5 diopters and about −10 diopters. In one embodiment, the net minus power of the peripheral region 214 is about −5 diopters. In this embodiment, if the central region has a power of +3 diopters, then the power of the peripheral region will be −8 diopters. If the central region has a power of +6 diopters, then the power of the peripheral region 214 will be −11 diopters.

In an embodiment in which the refractive error to be treated is astigmatism in addition to myopia or hyperopia. The surface area of the section comprising the central region 210 and the intermediate region 212 is chosen to be comprised between about 20% and about 40% of the surface area of the pupil 204 of the eye 202. As a result, the surface area of the peripheral region 214 is comprised between about 60% and about 80% of the surface area of the pupil 204. The power of the central region 210 is comprised between −0.25 diopter and −10 diopters of astigmatism. The power of the peripheral region 214 is comprised between about +3.75 diopters and about +20 diopters for myopic astigmatic subjects and between about −3.75 diopters and about −20 diopters for the hyperopic astigmatic subjects. In one embodiment, the net plus power of the peripheral region 214 is about +5 diopters.

In a first embodiment in which the refractive error to be treated is presbyopia, the central region 210 may be used for correcting the distance vision. In this case, the surface area of the section comprising the central region 210 and the intermediate region 212 is chosen to be comprised between about 20% and about 30% of the surface area of the pupil 204 of the eye 202, for a distance-centered design. As a result, the surface area of the peripheral region 214 is comprised between about 70% and about 80% of the surface area of the pupil 204. The power of the central region 210 is comprised between −30 diopter and +25 diopters. The add-power of the peripheral region 214 is comprised between about +0.25 diopters and about +5 diopters. In one embodiment, the add-power of the peripheral region 214 is about +2.5 diopters.

In a second embodiment in which the refractive error to be treated is presbyopia, the peripheral region 214 is used for correcting the distance vision. In this case, the surface area of the section comprising the central region 210 and the intermediate region 212 is chosen to be comprised between about 10% and about 30% of the surface area of the pupil 204 of the eye 202, for a near-centered design. As a result, the surface area of the peripheral region 214 is comprised between about 70% and about 90% of the surface area of the pupil 204. The power of the peripheral region 214 is comprised between −30 diopters and +25 diopters. The power of the central region 210 is chosen so that the central region 210 provides an add-power comprised between about +0.25 diopters and about +5 diopters. In one embodiment, the add-power of the peripheral region 114 is about +2.5 diopters.

In one embodiment, the correction of astigmatism may be incorporated with the correction of myopia or hyperopia, in the central region, extending to the peripheral region according to the designs described above.

In one embodiment, the correction of astigmatism can be incorporated with the correction of myopia or hyperopia, in the central region, but not into the peripheral region according to the designs described above.

In one embodiment, the correction of astigmatism may be incorporated with the correction of presbyopia in the peripheral region and/or in the central region.

High order aberrations are known to contribute to the deterioration of the visual acuity and may also influence the progression of refractive error. High order aberrations can be inherent to the optical components of the eye, and also of the optical device aiming to correct visual acuity. The medical device described herein generates negative spherical aberration if the power of the central region is negative, and positive spherical aberrations if it is positive.

In one embodiment, the present medical device may be designed so as to incorporate a variation of the power on its anterior surface to minimize the negative impact of its optical profile on myopia and axial length evolution. It may also incorporate a variation of the power of its anterior surface to optimize the positive impact of its optical profile on myopia and axial length management.

In one embodiment, the front surface of the medical device, with negative central region power, may be modified to reduce the negative spherical aberrations generated by its central region power.

In another embodiment, the front surface of the medical device with positive central region power may be modified to reduce the positive spherical aberrations generated by its central region power.

In a further embodiment, the front or the back surface of the medical device may be modified differently in each principal meridian to accommodate the presence of toric correction (for astigmatism)

In still another embodiment, the front surface of the medical device may be modified to reach a neutral level of spherical aberrations induced by the central region power in the case of presbyopic correction.

While the above description refers to a central region 110, 210 having a circular shape and an intermediate region 112, 212 and a peripheral region 114, 214 each having an annular shape, it should be understood that the central, intermediate and peripheral regions may have other shapes. For example, they may have an oval shape, a square shape, or the like as long as each region covers the above-defined percentage of the surface area of the pupil.

In one embodiment, the medical device 100, 200 is a corrective lens.

In one embodiment, the corrective lens is a contact lens adapted to be positioned on the ocular surface of the subject. In one embodiment, the contact lens is a soft lens. In another embodiment, the contact lens is a rigid, a gas permeable lens or a hybrid lens.

In another embodiment, the corrective lens is an intraocular lens.

In one embodiment, the medical device 100, 200 comprises a fourth annular region 116, 216 extending radially from the peripheral region 114, 214, respectively, and surrounding the peripheral region 114, 214. The width of the fourth region 116, 216 may be chosen so that the medical device 100, 200, respectively, covers at least the whole surface of the visible cornea. In an embodiment in which the medical device is designed for myopia, the power of the fourth region 116, 216 may be chosen so as to be greater than that of the peripheral region 114, 214. For example, the power of the fourth region 116, 216 may be between 1.0 diopter and 10 diopters greater than the power of the peripheral region 114, 214. In an embodiment in which the medical device is designed for hyperopia, the power of the fourth region 116, 216 may be chosen so as to be less convex or more concave than that of the peripheral region 114, 214. For example, the power of the fourth region 116, 216 may be between 1.0 diopter and 10 diopters less than the power of the peripheral region 114, 214.

It should be understood that the other characteristics of the medical device 100, 200, such as the curvature of the medical device, the width of the fourth region, if any, the material(s) of which the medical device 100, 200 is made, etc. may be determined according to the prior art methods.

In one embodiment, the fourth region is provided with a power constant over the whole surface area of the fourth region.

In another embodiment, the power is not constant in the fourth region and may vary through the fourth region. For example, the power associated to the fourth region may vary according to the angular position.

Figure 3:
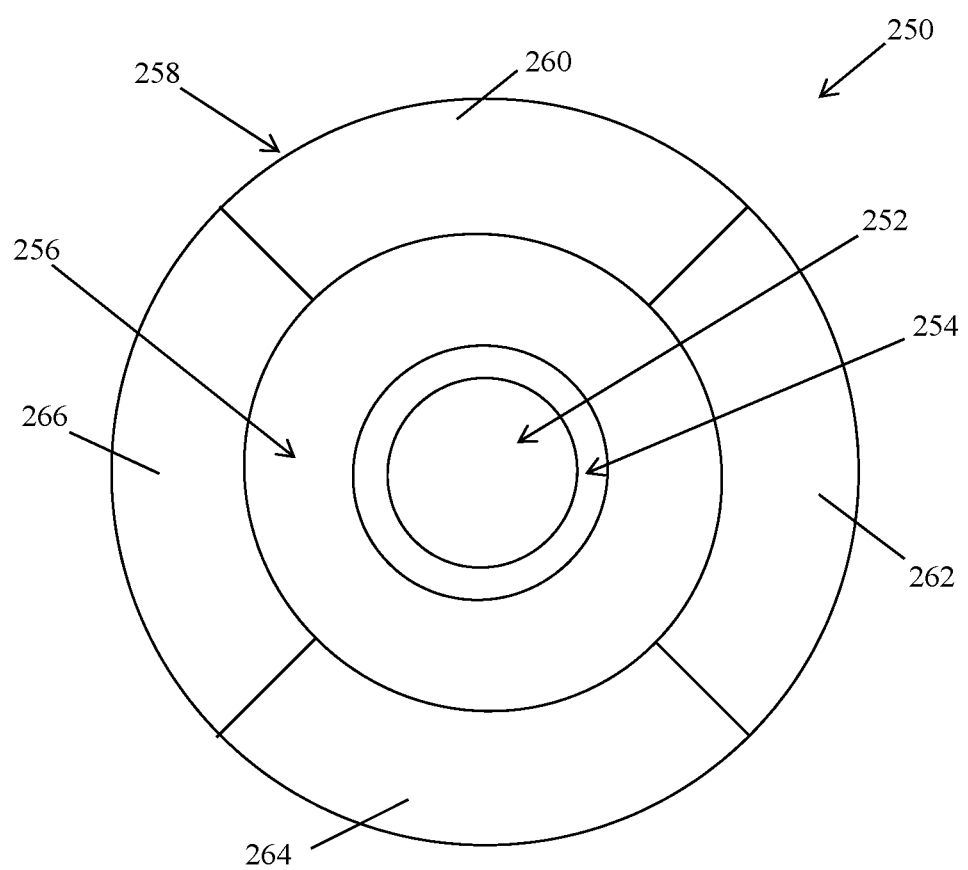
FIG. 3 illustrates a medical device for treating a refractive error comprising a central region, an intermediate region, a peripheral region and an external region, in accordance with an embodiment.

In one embodiment, the fourth region may be divided into at least two sections each having a respective power. FIG. 3 illustrates one embodiment of a medical device 250 for managing the axial length growth of an eye. The medical device 250 comprises a central region 252, an intermediary region 254 surrounding the central region 252, a peripheral region 256 surrounding the intermediary region 254 and a fourth or external region 258 surrounding the peripheral region 256. The central region 252 is provided with a first power and the peripheral region 256 is provided with a second and different power. As described above, the power of the peripheral region 256 may be determined according to a target net power using the power of the central region 252.

The external region 258 is divided into four angular sections or quadrants 260-266 which each have a respective power. The quadrants 260-266 may correspond to superior, nasal, inferior, and temporal quadrants. In the case of a right eye, the quadrants 260, 262, 264 and 266 may correspond to superior, nasal, inferior and temporal quadrants, respectively. In the case of a left eye, the quadrants 260, 262, 264 and 266 may correspond to superior, temporal, inferior and nasal quadrants, respectively. In one embodiment, the power of the quadrants 260-266 alternates between the power of the central region 252 and the power of the peripheral region 256 and two adjacent quadrants 260-266 are provided with a different power. For example, the quadrants 260 and 264 may be provided with the same power as that of the central region 252 while the quadrants 262 and 266 may be provided with the same power as that of the peripheral region 256.

While the external region 258 is divided into four sections 260-266, it should be understood that the number of angular sections may vary as long as the external region 258 comprises at least two sections. In one embodiment, the number of angular sections may be equal to an even number. For example, the number of quadrants may be four, eight, etc.

In one embodiment the medical device 250 may further comprise a transition region sandwiched between the peripheral region 256 and the external region 258. The thickness of the transition region may be chosen to be as thin as possible to offer an abrupt power transition between the peripheral region 256 and the external region 258. In one embodiment, the width of the transition region may at most equal to 1.5 mm.

In one embodiment, the medical device 250 may be designed with a central plus or minus power, with or without astigmatism. The external region 258 may have a higher or lower net power (for myopes) and various net powers (for hyperopes) in each of the four angular sections or quadrants. The angular sections may be regrouped by pairs and each pair of angular sections may have the same power. For example, the nasal and temporal quadrants may have a same first power while the superior and inferior quadrants may have a same second power different from the first power.

In one embodiment, the surface area of the area covered by the peripheral region 256, the external region 258 and optionally the transition region comprised between the peripheral region 256 and the external region 258, if any, corresponds to the percentage of the pupil associated with the above-presented peripheral region 116, 216, depending on the condition to be treated.

In one embodiment, the width of the peripheral region 256 is chosen to be minimal, e.g. comprised between about 0.1 mm and about 1.5 mm.

While the medical device 100, 200 comprises a peripheral region 116, 216 having an homogenous or constant power therethrough, the person skilled in the art would understand that the above-presented concept of dividing the external region 258 into a plurality of zones each having a respective power may be applied to a medical device provided with three regions, i.e. a central region, and intermediary region and a peripheral region, such as the medical device 100. For example, the peripheral region 116 may be divided into a plurality of angular sections or quadrants, each provided with a respective power. For example, the peripheral region 116 could comprise four quadrants such as superior, nasal, inferior and temporal quadrants.

In one embodiment, the power associated with each angular section of the peripheral region 116 may be equal to either the power of the central region 110 or the above-presented power for the peripheral region 116, and two adjacent angular sections may have different power values.

In one embodiment, the number of angular sections contained in the peripheral region 116 may be equal to an even number. For example, the number of quadrants may be four, eight, etc.

The person skilled in the art will understand that such a design comprising an external region having a varying power or the design comprising a peripheral region having a varying power may have intra-ocular applications and may also be applicable for laser surgeries.

For example, for myopic and/or astigmatism correction, the medical device may comprise a central region, an intermediary region, a peripheral region, an external region and optionally a transition region between the peripheral region and the external region, as described above. The surface area covered by the central and the intermediary regions may be comprised between about 20% and about 40% of the surface area of the pupil of the eye. The power of the peripheral region may be comprised be comprised between about +3.75 diopters and about +20 diopters depending on the target net power and the power of the central region. The surface are covered by the central intermediary and peripheral regions may correspond to the surface are of the pupil. The external region comprises an even number of power alternating angular sections of the which the power is either equal to the power of the central region or the power of the peripheral region. The width of the intermediary region and that of the transition region, if any, may be comprised between 0.1 mm and 1.5 mm to provide an abrupt power transition. Such a design may ensure that the percentage of peripheral defocus is stable even if the diameter of the pupil increases in darker condition. Also, such a design may decrease the spherical aberration created in darker condition, thereby improving the visual acuity.

For example, a patient having a photopic pupil diameter of 5.0 mm may need a design with a central region of 2.24 mm in diameter surrounded by an annular intermediary region of 0.5 mm, an annular peripheral region of 1.4 mm wide and an external region of 3.36 mm wide comprising sections having the power of either the central region or that of the peripheral region. For example, the external region may comprise 8 angular sections of which four sections have the same power as that of the central region, the other four sections have the same power as that of the peripheral region and no adjacent section have the same power. This design could be applied to a lens having an optical zone of 8.0 mm in diameter and may provide 74% of peripheral defocus even in darker condition.

In another example, the same design can be applied to hyperopia. In this case, the surface are of the central and intermediary regions is comprised between 30% and 50% of the pupil area. The peripheral region is provided with a power comprised between −3.75 diopters and −20 diopters.

In an embodiment in which the medical device 100, 200 is a soft contact lens, some parameters of the soft lens may be personalized for each subject. For example, the base curve of the lens, the overall diameter, the power of the central region 110, 210, the percentage of the pupil to be covered by the peripheral region 114, 214 and the width of the intermediate region 112, 212 may be adjusted for each patient. Other parameters may not vary from one subject to another. For example, the type of lens, the net power determined to control myopia and axial length progression, the optical zone diameter (i.e. the diameter of the section comprising the central, intermediate and peripheral regions), the width of the intermediate region 112, 212, the peripheral curve, the material(s) of which the medical device 100, 200 is made, etc. may be constant from one subject to another.

In an example in which the lens is designed to treat myopia, the base curvature may be determined based on the effective curvature reading of the cornea of the subject and a flattening factor related to the final lens diameter. If the lens comprises a myopia management strategy portion, the base curvature may be steepened by 0.1 mm to optimize its centration and its stability. In one embodiment, the curvature and diameter of the medical device 100, 200 is adjusted to generate a sagittal depth vaulting over the sagittal height of a given ocular surface by a value varying from about 100 microns (um) up to about 300 microns (um) maximum.

The overall diameter of the lens may be established about 2 mm over the visible corneal horizontal diameter as measured with topography, biometry or any other adequate optical method. The power of the central region 110, 210 may be determined according to the cycloplegic refraction of the eye of the subject or other valuable means to assess the refractive components. The percentage of the pupil to be covered by the peripheral region 114, 214 may be determined as a function of each subject to influence the peripheral defocus and consequently the ocular axial length growth. A series of medical devices can be designed where the percentage of the pupil to be covered varies, based on the patient's parameters as described below In an example in which the lens is designed to treat myopia, the type of lens may be a distance-centered bifocal soft contact lens. The net power may be equal to +5.00 diopters independently of the subject. The optical zone diameter (i.e. the diameter of the region comprising the central, intermediate and peripheral regions) may be fixed at 8 mm independently of the subject. The width of the intermediate region 112, 212 may be fixed at 0.5 mm independently of the subject and the intermediate region 112, 212 may be designed, with a sharp, fast and abrupt power transition where the power slope is the steepest possible. The peripheral curves, from the end of the peripheral region to the edge of the medical device, may be chosen to be standard to favor lens centration and tear exchange. Finally, in the case of soft lenses, the lens may be made of hydrogel or silicone hydrogel, or any new material approved for such usage, which is disposable (lasting 1 day to 6 months) or conventional (lasting >6 months) independently of the subject. Rigid lenses may be made of polymethylmethoacrylate (PMMA), and gas permeable material may be made of acrylate, silicone, or Fluor (or a combination of 2 or 3 of these materials) or any new material approved for such usage. Hybrid lenses may be made of a combination of gas permeable material and hydrogel or silicon-hydrogel or any new material approved for such usage.

Figure 4:
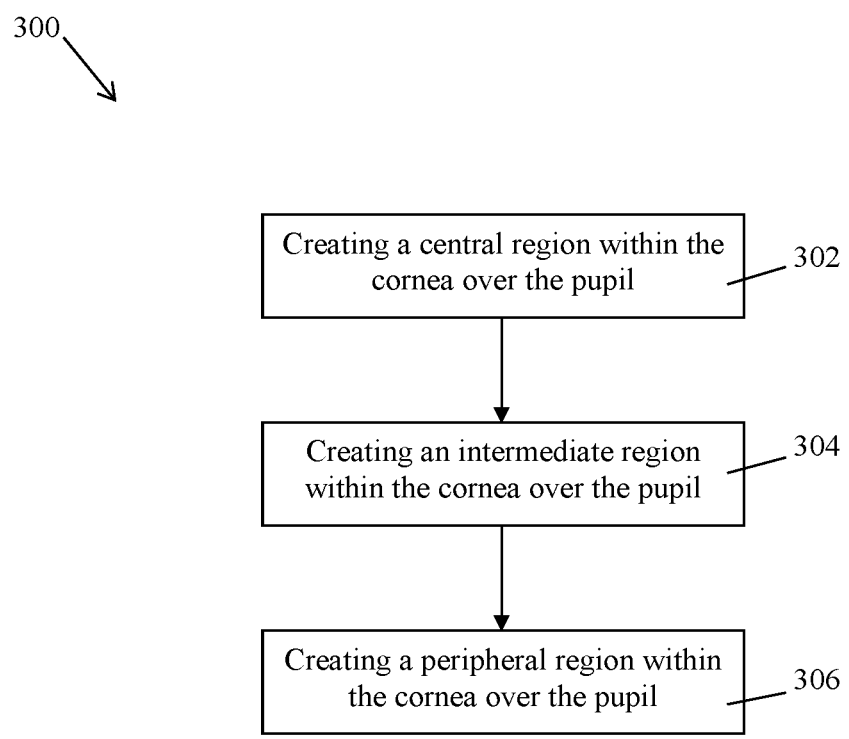
FIG. 4 is a flow chart of a medical method for treating a refractive error, in accordance with an embodiment.

The above-described medical device 100, 200 may be embodied as a method 300 of medical treatment of a refractive error such as myopia, hyperopia, astigmatism or presbyopia, as illustrated in FIG. 4.

The first step 302 consists in creating a central region within the cornea of the eye of a subject. The central region is circular and centered on the pupil so that the center of the central region substantially overlaps with the center of the pupil. The central region is created using an adequate energy source that modifies the corneal shape within the defined central region in order to remove a given thickness of the cornea. As described below, the surface area of the central region is chosen so that the central region covers a given percentage of the surface area of the pupil. The thickness of the cornea to be removed is defined as a function of a desired power for the central region.

In one embodiment, the source of energy used for modifying the corneal shape is a laser. In another embodiment in which hyperopia is to be managed, the energy source may be a source of heat adapted to apply heat to the periphery of the cornea.

The second step 304 consists in creating an intermediate region within the cornea of the eye. The intermediate region has an annular shape and extends radially from the central region while surrounding the central region. The intermediate region of the cornea is created using the energy source by cutting a given thickness of the cornea within the intermediate region. The surface area of the intermediate region is chosen so that the intermediate region covers a given percentage of the surface area of the pupil.

The last step 306 consists in creating a peripheral region within the cornea of the eye. The peripheral region has an annular shape and extends radially from the intermediate region while surrounding the peripheral region. The peripheral region of the cornea is created using the energy source by cutting a given thickness of the cornea within the intermediate region so that the peripheral region be provided with a desired power. The surface area of the peripheral region is chosen so that the peripheral region covers a given percentage of the surface area of the pupil.

In one embodiment, the energy source used at steps 302, 304 and 306 for creating the central, intermediate and peripheral regions is a laser. In one embodiment, the laser is an excimer laser. In another embodiment, the laser is a femtosecond laser.

In one embodiment, the method 300 further comprises a step of removing a layer of the epithelium before performing step 302. The surface area of the removed epithelium corresponds at least to the surface area of the region covered by the central, intermediate and peripheral regions. Once the epithelium region has been removed, the central, intermediate and peripheral regions are created. In one embodiment, an excimer laser is used for removing the epithelium and creating the central, intermediate and peripheral regions. When at least a layer of the epithelium is removed, the method 300 corresponds to a Photorefractive Keratectomy surgery. It should be understood that any adequate method for removing at least a layer of the epithelium may be used. For example, a microkeratome may be used for removing at least a layer of the epithelium. In another example, a laser such as a femtosecond laser may be used.

In another embodiment, a flap is created and bent before performing the creation of the central, intermediate and peripheral regions. Once the three regions have been created, the flap is positioned back to its initial position. The surface area of the flap corresponds at least to the surface area of the region covered by the central, intermediate and peripheral regions. In one embodiment, a microtome blade is used for creating the flap. In another embodiment, a laser such as femtosecond laser is used for creating the flap. The laser beam is then focused just below the epithelium and gases are emitted by the underlying cell when they evaporate, thereby creating an air-type layer from which the upper cornea can detach. When a flap is created, the method 300 corresponds to an In Situ Keratomileusis (LASIK) surgery.

In one embodiment, the peripheral region created at step 306 extends beyond the pupil so that the end of the pupil is lying under the peripheral region. In this case, the peripheral region comprises a first section which overlaps the pupil and a second section which is located outside of the pupil. In one embodiment, the power of the first section may be different from that of the second section to provide the adequate power for the peripheral region.

In an embodiment in which a laser is used, the central, intermediate and/or peripheral regions may be created point-by-point based on the topography of the cornea in order to reduce high order aberrations.

It should be understood that the surgical method 300 may be used for the correction of myopia, hyperopia, astigmatism and/or presbyopia.

The surface area of the three different regions is chosen as a function of the surface area of the photopic pupil of the eye to be treated. The surface area of each region is chosen so as to cover a given percentage of the surface area of the pupil. The percentage of the surface area of the pupil covered by each region, the power of the central region and the power of the peripheral region are chosen as a function of the refractive error to be treated and characteristics of the subject such as the dimensions (diameter) of the pupil of the subject and the cycloplegic refraction of the eye of the subject. For any refractive error and any subject, the power of the peripheral region is comprised between about +3.75 diopters and about +20 diopters or between about −3.75 diopters and about −20 diopters, or chosen so that the peripheral region provides an add-power comprised between +0.25 and +5.00 diopters. Alternatively, the power of the central region may be chosen so that the central region provides an add-power comprised between +0.25 and +5.00 diopters. Furthermore, the width of the intermediate region is chosen to be minimal, e.g. at most equal to 1.5 mm to ensure an abrupt variation of power between the central and peripheral regions.

In an embodiment in which the refractive error to be treated is myopia with or without astigmatism, the surface area of the section comprising the central region and the intermediate region is chosen to be comprised between about 20% and about 40% of the surface area of the pupil of the eye. As a result, between about 60% and about 80% of the surface area of the pupil 204 is covered by the peripheral region. The power of the peripheral region is comprised between about +3.75 diopters and about +20 diopters so that the net power be comprised between about +5 diopters and about +10 diopters. In one embodiment, the net plus power of the peripheral region is about +5 diopters.

In an embodiment in which the refractive error to be treated is hyperopia with or without astigmatism, the growth of the ocular axial length is to be increased. The surface area of the section comprising the central region and the intermediate region is chosen to be comprised between about 30% and about 50% of the surface area of the pupil of the eye. As a result, the surface area of the peripheral region is comprised between about 50% and about 70% of the surface area of the pupil. The power of the central region is comprised between +0.25 diopter and +25 diopters. The power of the peripheral region is comprised between about −3.75 diopters and about −20 diopters. In one embodiment, the net minus power of the peripheral region is about −5 diopters.

In an embodiment in which the refractive error to be treated is astigmatism, the surface area of the section comprising the central region and the intermediate region is chosen to be comprised between about 20% and about 40% of the surface area of the pupil of the eye. As a result, the surface area of the peripheral region is comprised between about 60% and about 80% of the surface area of the pupil. The power of the central region is comprised between −0.25 diopter and −10 diopters for the astigmatic component. The power of the peripheral region is comprised between about +3.75 diopters and about +20 diopters so that the net power be comprised between +5 diopters and +10 diopters. In one embodiment, the net plus power of the peripheral region is about +5 diopters.

In a first embodiment in which the refractive error to be treated is presbyopia, the central region may be used for correcting the distance vision. In this case, the surface area of the section comprising the central region and the intermediate region is chosen to be comprised between about 20% and about 30% of the surface area of the pupil of the eye. As a result, the surface area of the peripheral region is comprised between about 70% and about 80% of the surface area of the pupil. The power of the central region is comprised between −30 diopter and +25 diopters. The add-power of the peripheral region is comprised between about +0.25 diopters and about +5 diopters. In one embodiment, the add-power of the peripheral region is about +2.5 diopters.

In a second embodiment in which the refractive error to be treated is presbyopia, the peripheral region is used for correcting the distance vision. In this case, the surface area of the section comprising the central region and the intermediate region is chosen to be comprised between about 10% and about 30% of the surface area of the pupil of the eye. As a result, the surface area of the peripheral region is comprised between about 70% and about 90% of the surface area of the pupil. The power of the peripheral region is comprised between −30 diopters and +25 diopters. The power of the central region is chosen so that the central region provides an add-power comprised between about +0.25 diopters and about +5 diopters. In one embodiment, the add-power of the peripheral region is about +2.5 diopters.

As for the medical device 100, 200, the central region created at step 302 may have a circular shape and the intermediate and peripheral regions created at step 304 and 306, respectively, may have an annular shape. However, the person skilled in the art will understand that other shapes may be contemplated. For example, the different regions created by the method 300 may have an oval shape, a square shape, or the like as long as each region covers the above-defined percentage of the surface area of the pupil.

In the following there is described a method for designing a medical device for managing the axial length growth of an eye of a subject. The user of the method may be an optometrist, an ophthalmologist, an optician, or the like. The present method allows for customizing the design of the medical device to the subject.

The user is presented with a set of predefined designs of medical devices. The set of predefined designs comprises at least two different partial designs for the medical device and the user selects an adequate partial design as a function of the needs of the subject for which the medical device is to be designed. It should be understood that a partial design of a medical device comprises only some of the characteristics required for designing the medical device. The characteristics of the medical device that are not specified in the partial design are to be chosen by the user as a function of some characteristics of the subject.

In one embodiment, the partial designs of the medical device each comprise a predefined percentage of the surface area of the pupil to be covered by the central region and the intermediate region of the medical device. For example, three partial designs may exist when myopia is to be treated. In this case, the first partial design of the medical device may include a first value for the percentage of the pupil to be covered by the section defined by the central and intermediate regions that is comprised between 35% and 40%. The second partial design of the medical device may include a second value for the percentage of the pupil to be covered by the section defined by the central and intermediate regions that is comprised between 30% and 35%. The third partial design of the medical device may include a third value for the percentage of the pupil to be covered by the section defined by the central and intermediate regions that is comprised between 20% and 30%.

In another example in which hyperopia is to be treated, three partial designs may also exist. In this case, the first partial design of the medical device may include a first value for the percentage of the pupil to be covered by the section defined by the central and intermediate regions that is comprised between 40% and 50%. The second partial design of the medical device may include a second value for the percentage of the pupil to be covered by the section defined by the central and intermediate regions that is comprised between 35% and 40%. The third partial design of the medical device may include a third value for the percentage of the pupil to be covered by the section defined by the central and intermediate regions that is comprised between 30% and 35%.

In a further example in which presbyopia is to be treated and in which the central region is used for correcting the distance vision (distance-centered design), two partial designs may also exist. In this case, the first partial design of the medical device may include a first value for the percentage of the pupil to be covered by the section defined by the central and intermediate regions that is comprised between 25% and 30%. The second partial design of the medical device may include a second value for the percentage of the pupil to be covered by the section defined by the central and intermediate regions that is also comprised between 20% and 25% but different from the first value.

In still a further example in which presbyopia is to be treated and in which the central region is used for correcting the near vision (near-centered design), three partial designs may also exist. In this case, the first partial design of the medical device may include a first value for the percentage of the pupil to be covered by the section defined by the central and intermediate regions that is comprised between 25% and 30%. The second partial design of the medical device may include a second value for the percentage of the pupil to be covered by the section defined by the central and intermediate regions that is also comprised between 20% and 25%. The third partial design of the medical device may include a third value for the percentage of the pupil to be covered by the section defined by the central and intermediate regions that is comprised between 10% and 20%.

The user of the method selects the adequate partial design as a function of the subject, i.e. selects the adequate percentage of the pupil to be covered by the section comprising the central and intermediate regions as a function of the subject.

In one embodiment, the partial design is selected by calculating the percentage of the pupil to be covered by the section comprising the central and intermediate regions as follows:

square root of distance zone of (%) X pupil diameter, for soft lenses; and square root of (%) X pupil diameter+$\beta$, for gas permeable lenses, where $\beta$ represents a value of power distribution. For example, given a pupil diameter of 5.50 mm, the formulation to estimate 20% coverage would be given by square foot (0.2)×5.5. The result would be 2.46 mm. For a 40% coverage, the equation would be: square root (0.4)×5.5 mm=3.48 mm The selection of the adequate partial design may also be dictated by the history of the refractive error progression of the subject. Fast progressors may benefit from smaller central zone (around 20%) and a high net power value (>+5.00 diopters), which implies a peripheral power value of a higher convex power as well. More stable patients may be better suited if fitted with larger central zone and a medium peripheral power value. For example, a −5 diopter myope, progressing moderately, may be fitted with a 30% to 40% coverage and a +5 diopters net power value, which implies a peripheral region power value of +10 diopters. The intermediary region may have a width at most equal to 1.5 mm, e.g. between 0.1 mm to 1.5 mm depending on the manufacturing facility. In another example, a −6 diopters myopic subject, known as fast progressing, may be fitted with a 20% coverage and net power value comprised between +8 diopters and +10 diopters. Consequently, the peripheral region power would be +14 diopters to +16 diopters and the intermediary region would have a width at most equal to 1.5 mm, e.g. between 0.1 mm to 1.5 mm.

The quality of the distance vision may also dictate which partial design may be used. For example, if a myopic subject, fitted with a small distance zone and a high peripheral power value, complaints about blurred vision at distance, the next lens to try may be mid-distance zone with the same peripheral power value, or a small distance zone with a reduced peripheral power value. For example, a −3.5 diopters myopic subject fitted with a 30% central region design and a +5 diopters net power for the peripheral region, can be refitted with a −3.5 diopters with a 40% central region and the same +5 diopters net value, or with a −3.50 diopters with a 30% central region and a +3 diopters net power for the peripheral region. In the first case, the peripheral region power would be +8.5 diopters and in the second case, +6.5 diopters.

The value for the power of the central region, the net power value and, consequently the power value of the peripheral region are to be determined by the user of the method as a function of the characteristics of the subject, thereby customizing the design of the medical device to the subject. Once the partial design has been selected and the value for the power of the central region, the net power and the power value of the peripheral region have been determined, the design of the medical device is complete.

In one embodiment, the surface area of the pupil of the subject to be treated is measured. For example, the surface area of the pupil may be assessed in photopic condition with uncovered eyes, with calculation based on its radius ($S=\pi \times r^2$) when the subject is looking at distance. The surface of the distance zone is determined by $S_2$=(square root (%)×r). For example, the formulation for a coverage of 30% would be S=square root (0.3)×r, where r is the diameter of the pupil divided by 2.

In one embodiment, the surface area or diameter of the pupil may be determined using a database. For example, the database may comprise an average pupil diameter for given populations. The diameter of the pupil that corresponds to the subject is retrieved by determining to which population the subject to be treated belongs. The user also has to measure the surface area of the eye of the subject. An exemplary population may correspond to Caucasian patients from 6 to 9 years old to which an average pupil diameter is associated. Another exemplary population may correspond to East Asian patients from 10 to 14 years old.

While in the above description the partial designs each comprises a predefined percentage of the surface area of the pupil to be covered by the central region and the intermediate region of the medical device and the user is requested to determine the power value for the central and peripheral regions, the person skilled in the art would understand that the partial designs may each comprise a predefined net power value. In this case, the user selects the adequate partial design as a function of the subject, i.e. selects the adequate predefined net power value as a function of the subject, and determines the percentage of the surface area of the pupil to be covered by the central region and the intermediate region of the medical device as a function of the characteristics of the subject, thereby customizing the design of the medical device to the subject.

In one embodiment, the first partial design to be selected for a particular eye should be the one that offers the minimal central region, without impaction vision at distance, considering the overall pupil surface area. For myopic and hyperopic subjects, in the case of blur at distance, the next partial design to be selected should be the first one available with a larger central zone. If the refractive error evolves, then the next partial design to fit is the first one available with a smaller central zone.

In the following the experimental results of an investigation on a medical device designed to manage ocular axial length growth in the context of refractive error evolution are presented. In particular, the results indicate the effectiveness of the medical device in young myopic patients Purpose This study was conducted to test the effectiveness of a medical device, more specifically a soft multifocal contact lens, designed according to the above presented principles, in controlling the progression of the refractive error and the elongation of the axial length in a group of young myopic patients.

Method

This is a prospective randomized, cross-over study following 22 patients aged from 7 to 12 years old, who exhibited progressive myopia. This study was made at Clinique Universitaire de la Vision of Université de Montreal, after approval of the ethics committee Internal Research Bureau. One intervention was used and compared with a control. Rates of myopia evolution and axial length growth were estimated on an annual basis and compared between intervention and the control.

Patient Selection

Patients were included in this study if they met the following criteria: (1) at least −1 diopter of myopia, but no more than −4 diopters; (2) confirmed progression of at least −0.25 diopter in either principal meridian in either eye in the past 6 months; (3) refractive astigmatism less than −1 diopter; (4) best corrected visual acuity of 20/20 each eye; (5) no myopia control strategy or device in the last 6 months; (6) no binocular vision disorder; (7) good ocular health; (8) no intake of any medication with a potential to affect visual acuity or the tear film stability; (9) no contra-indication to contact lens wear; (10) no known allergy to any product used in this study; (11) able to understand the purpose and the schedule of the clinical study; and (12) patient's parents or legal guardians provided an informed consent signed form.

This study includes 5 visits during 1 year: (1) baseline data acquisition and contact lenses ordering; (2) delivery of the lenses; (3) control examination at 14 days; (4) control examination at 180 days; (5) delivery of new lenses; and (6) final control at 360 days. During visit one, comprehensive ocular examination was conducted, including in particular (1) case history with emphasis on risk factors for myopia evolution, past methods of correction, and pattern of evolution (2) visual acuity assessment aided and unaided, at distance and at near (3) cover test at distance and at near through current optical correction (4) evaluation of the eye deviation at near, using the phoropter (5) evaluation of the accommodative convergence/accommodation ratio using a gradient method, with the phoropter (6) evaluation of the accommodative lag at near, using a retinoscope (7) pupil diameter measurement in photopic and scotopic condition, using an electronic pupilllometer (8) pupillary reflex, using a pen light at near (9) corneal tomography using a Schiempflug based tomograph (10) high order aberrations evaluation, using a Hartman-Schack type aberrometer (11) axial length measurement using an infra-red biometer (12) refraction using an electronic auto-refractor and repeat of the same measurement after instillation of 2 drops of cyclopentolate 1% drops in each eye (e.g. 25 minutes post instillation) (13) anterior segment assessment using a slit lamp and (14) intra-ocular pressure and corneal hysteresis measurement using an ocular response analyzer.

At the end, one eye was selected randomly to be fitted with the medical device (intervention) and the fellow eye with a monofocal soft contact lens made of the same material, serving as control. Both lenses were designed and ordered on the basis of the corneal profile and its parameters, cycloplegic refraction and pupil area.

More specifically, the medical device comprises a central region having a power equivalent to the cycloplegic refraction value as measured, a transition region surrounding the central region and having a width of approximatively 1.0 mm, and a peripheral region having a +5 diopters add-power, wherein a surface area of each one of the central and peripheral regions is chosen for each patient as a function of the surface area of the pupil of the eye. The control lens is made of a single central region having a power equivalent to the cycloplegic refraction and with a width of 6 mm. This region is surrounded by peripheral regions with no effective power. The overall diameter of the lenses is selected as a function of the corneal diameter as established by tomographic evaluation. The central curve of the lens is selected as a function of the average central curvature of the cornea. Each pair of lenses was consequently fully customized to the patient.

At visit 2, lens orders were checked and delivered to the patient. The following testing was performed with contact lenses in place: (1) evaluation of the lens fitting (position and movement) using a slit lamp. If lenses were evaluated as not adequate, another set of contact lenses was ordered based on this evaluation. If the lenses were found correct: (2) distance and near visual acuity, using a C Landolt chart in photopic condition (2) over-refraction at distance using a phoropter (3) eye deviation evaluation (phoria) at distance and at near using the phoropter (4) topography over the lenses using a tomograph (5) high order aberrations measurement using a Hartman-Schack type aberrometer (6) insertion and removal instructions given to patient and his parents (7) recommendations for contact lens care and schedule for the next appointment.

At visit 3, a partial ocular examination was conducted, including (1) case history related to the wear of the study lenses provided 14 days earlier (2) visual acuity at distance and at near, with lenses in place (3) evaluation of the lenses on the eye, and after their removal, ocular health assessment using a slit lamp (4) recommendations to the patient and schedule for the next appointment.

At visit 4, a partial ocular examination was conducted, including (1) case history (2) visual acuity measurement, at distance and at near, with lenses in place (3) over-refraction at distance using the phoromether (4) evaluation of the eye deviation at near (phoria), accommodative convergence/accommodation ratio, using a phoropter, and accommodative lag using a retinoscpoe (5) pupillary diameter evaluation using an electronic pupilometer (6) subjective refraction at distance, without contact lenses, using the phoropter (7) anterior segment assessment using the slit lamp (8) axial length measurement using infra-red biometer (9) corneal tomography using a Scheimpflug-type tomograph (10) auto-refraction using an electronic auto-refractor, after instillation of 2 drops of cyclopentolate 1% (e.g. 25 minutes post instillation) (11) ocular fundus examination under dilation, using magnifying lenses and a slit lamp. New lenses were designed and ordered to respect the cross-over protocol. This means that the eye firstly fitted with the medical device was now fitted with a monofocal lens, and to the contrary, the eye firstly fitted with the monofocal lens was equipped with the medical device. Both lenses were customized to each eye of the patient as previously described.

At visit 5, new lenses were delivered and a partial ocular examination was conducted, including (1) a brief case history (2) visual acuity at distance and at near with contact lenses on the eyes (3) slit lamp assessment of the lenses and of the anterior segment (4) recommendations to the patients and review of the care regimen. Next appointment schedule was also discussed.

At visit 6, a partial ocular examination was conducted, including the same testing procedures made at the initial visit.

Three patients did not show up at the last visit and another three were excluded because they did not comply with the wearing schedule of lenses during the study. A complete data set was obtained from 16 patients in total.

Results

On average, in 6 months, the eye wearing the medical device evolved by −0.16+0.24 diopter (−0.32 diopter projected on a yearly basis) and axial length grew by +0.14+0.10 mm, while the eye equipped with the control evolved by −0.32+0.33 diopter (−0.64 diopter yearly) and +0.15+0.13 mm respectively. There is a significant difference for myopia evolution when the medical device is compared to the control, representing a rate of 50% efficacy at 6 months and 61% at one year. For the axial length, there is a significant difference for the eye fitted with the control first, then wearing the medical device for the last 6 months (+0.16 mm with control then 0.10 mm with the medical device). The same effect was not observed for the eye fitted first with the medical device (+0.13 mm) then wearing the control (+0.17 mm).

Conclusions

The medical device as designed was effective to control myopia evolution and was also efficient to control axial length growth when the eye was firstly fit with the control lens.

The embodiments of the invention described above are intended to be exemplary only. The scope of the invention is therefore intended to be limited solely by the scope of the appended claims.

We claim:

1. A medical device for an eye of a subject, the eye having a pupil, the medical device comprising:
   a central region having a first power;
   a transition region surrounding the central region and having a width at most equal to 1.5 mm; and
   a peripheral region surrounding the transition region, the peripheral region having a second power chosen based on the first power to achieve a target net power associated with the peripheral region, the target net power being the addition of the first power and the second power,
wherein a surface area of each one of the central and peripheral regions is chosen as a function of a surface area of the pupil of the eye, and wherein a variation of a third power within the transition region is steep between the first power and the second power so that the transition region generates no optically usable power.

2. The medical device of claim 1, wherein the central and peripheral regions are adapted to treat at least one of myopia and astigmatism, and wherein a surface area of the central region and the transition region is comprised between about 20% and about 40% of the surface area of the pupil of the eye.

3. The medical device of claim 2, wherein the first power of the central region is comprised between about −0.25 diopter and about −30 diopters for said myopia and between about −0.25 diopter and about −10 diopters for said astigmatism.

4. The medical device of claim 3, wherein the target net power is comprised between about +3.5 diopters and about +10 diopters, and the second power is comprised between about +3.75 diopters and about +20 diopters.

5. The medical device of claim 4, wherein the target net power is equal to about +5 diopters.

6. The medical device of claim 1, wherein the central and peripheral regions are adapted to treat presbyopia.

7. The medical device of claim 6, wherein the medical device corresponds to a distance-centered device, and a surface area of the central portion and the transition portion is comprised between about 20% and about 30% of the surface area of the pupil of the eye.

8. The medical device of claim 7, wherein the first power of the central region is comprised between about −30 diopters and about +25 diopters, and the peripheral region is provided with an add-power comprised between about +0.25 diopter and +5 diopters.

9. The medical device of claim 8, wherein the add-power of the peripheral region is equal to about +2.5 diopters.

10. The medical device of claim 6, wherein the medical device corresponds to a near-centered device, and a surface area of the central portion and the transition portion is comprised between about 10% and about 30% of the surface area of the pupil of the eye.

11. The medical device of claim 10, wherein the second power of the peripheral region is comprised between about −30 diopters and +25 diopters, and the central region is provided with an add-power comprised between about +0.25 diopters and about +5 diopters.

12. The medical device of claim 11, wherein the add-power of the central region is equal to about +2.5 diopters.

13. The medical device of claim 1, wherein the peripheral region comprises a plurality of angular sections each having a respective power and two adjacent ones of the plurality of angular sections are provided with different powers.

14. The medical device of claim 13, wherein the respective power is equal to one of the first power of the central region and the second power of the peripheral region.

15. The medical device of claim 1, further comprising an external region surrounding the peripheral region.

16. The medical device of claim 15, further comprising a transition region comprised between the peripheral region and the external region, a width of the transition region being at most equal to about 1.5 mm.

17. The medical device of claim 15, wherein the external region comprises a plurality of angular sections each having a respective power, and wherein two adjacent ones of the plurality of angular sections are provided with different powers.

18. The medical device of claim 17, wherein the respective power is equal to one of the first power of the central region and the second power of the peripheral region.

19. The medical device of claim 17, wherein the external region is divided into an even number of said angular sections.

20. The medical device of claim 1, wherein the medical device is a corrective lens, the corrective lens being one of a contact lens and an intraocular lens.

* * * * *